(12) United States Patent
Zhang et al.

(10) Patent No.: US 6,453,648 B1
(45) Date of Patent: *Sep. 24, 2002

(54) METHOD FOR MANUFACTURING A HEAT GENERATING APPARATUS

(75) Inventors: Jie Zhang, Salt Lake City, UT (US); Hao Zhang, Midvale, UT (US); Larry Rigby, Salt Lake City, UT (US); Wade A. Hull, Taylorsville, UT (US)

(73) Assignee: Zars, Inc., Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/347,963

(22) Filed: Jul. 6, 1999

(51) Int. Cl.$^7$ ................................................. A61F 7/00
(52) U.S. Cl. ....................................................... 53/469
(58) Field of Search ....................... 252/182.29, 183.12, 252/962; 607/76, 114; 53/469, 474, 477

(56) References Cited

U.S. PATENT DOCUMENTS

| | | | | |
|---|---|---|---|---|
| 2,573,791 A | * | 11/1951 | Howells | 128/82.1 |
| 3,929,131 A | | 12/1975 | Hardwick | |
| 3,976,049 A | * | 8/1976 | Yamashita | 126/263 |
| 4,106,477 A | * | 8/1978 | Feld | 126/263 |
| 4,106,478 A | * | 8/1978 | Higashijima | 126/263 |

(List continued on next page.)

FOREIGN PATENT DOCUMENTS

| | | |
|---|---|---|
| GB | 2 163 956 A | 12/1988 |
| WO | 88/09169 | 1/1988 |
| WO | WO 97/01310 | 1/1997 |
| WO | WO 97/01311 | 1/1997 |
| WO | WO 97/01312 | 1/1997 |

(List continued on next page.)

OTHER PUBLICATIONS

Arky, et al., *Physicians' Desk Reference*, 1997, pp. 1336–1340.
Mack Publishing Company, "Stability of Pharmaceutical Products," *Pharmaceutical Sciences*, pp. 1481–1482, 1985.
McCafferty, et al., "Comparative In Vivo and In Vitro Assessment of the Percutaneous Absorption of Local Anaesthetics," *British Journal of Anaesthesia*, vol. 60, (1988), 64–69.
Woolfson, et al., "Concentration–Response Analysis of Percutaneous Local Anaesthetic Formulations," *British Journal of Anaesthesia*, vol. 61, (1988), pp. 589–592.
McCafferty, et al., "In Vivo Assessment of Percutaneous Local Anaesthetic Preparations," *British Journal of Anaesthesia*, vol. 62, (1989), pp. 17–21.

(List continued on next page.)

*Primary Examiner*—Rinaldi I. Rada
*Assistant Examiner*—Christopher Harmon
(74) *Attorney, Agent, or Firm*—Kirton & McConkie; Michael F. Krieger

(57) ABSTRACT

The present invention relates to a method for manufacturing a heating device which is capable of generating heat when exposed to oxygen. The heat generating element comprises activated carbon and iron is used to generate an exothermic oxidation reaction within the heating device. Introducing an oxidation inhibitor during the manufacturing process allows the manufacturing of the device to take place in ambient atmospheric conditions. The present invention also includes a loading facilitator which allows the heat generating medium to be more easily and efficiently loaded into the heat generating device. When appropriate, the oxidation inhibitor and loading facilitator can be removed.

17 Claims, 1 Drawing Sheet

U.S. PATENT DOCUMENTS

| | | | | |
|---|---|---|---|---|
| 4,114,591 A | * | 9/1978 | Nakagawa | 126/263 |
| 4,205,685 A | * | 6/1980 | Yoshida et al. | 128/399 |
| 4,210,670 A | | 7/1980 | Cooke | 424/324 |
| 4,230,105 A | | 10/1980 | Harwood | |
| 4,286,592 A | | 9/1981 | Chandrasekaran | |
| 4,366,804 A | * | 1/1983 | Abe | 126/263 |
| 4,529,601 A | | 7/1985 | Broberg et al. | |
| 4,685,911 A | | 8/1987 | Konno et al. | |
| 4,693,706 A | | 9/1987 | Ennis, III | |
| 4,747,841 A | | 5/1988 | Kuratomi et al. | |
| 4,830,855 A | | 5/1989 | Stewart | |
| 4,898,592 A | | 2/1990 | Latzke et al. | |
| 4,911,707 A | | 3/1990 | Heiber et al. | |
| 4,913,957 A | | 4/1990 | Strack et al. | |
| 4,925,743 A | * | 5/1990 | Ikeda et al. | 428/702 |
| 4,963,360 A | | 10/1990 | Argaud | |
| 4,994,049 A | | 2/1991 | Latzke et al. | 604/307 |
| 5,046,479 A | * | 9/1991 | Usui | 126/204 |
| 5,108,710 A | | 4/1992 | Little et al. | 422/104 |
| 5,114,411 A | | 5/1992 | Haber et al. | 604/203 |
| 5,128,137 A | | 7/1992 | Müller et al. | 424/449 |
| 5,147,339 A | | 9/1992 | Sundström | 604/307 |
| 5,213,129 A | | 5/1993 | Someah et al. | 137/101.11 |
| 5,217,718 A | | 6/1993 | Colley et al. | 424/449 |
| 5,229,133 A | | 7/1993 | Wright et al. | 424/473 |
| 5,233,981 A | * | 8/1993 | Miyashita | 607/114 |
| 5,276,032 A | | 1/1994 | King et al. | 514/239 |
| 5,279,594 A | | 1/1994 | Jackson | 604/265 |
| 5,329,976 A | | 7/1994 | Haber et al. | 141/25 |
| 5,330,452 A | | 7/1994 | Zook | 604/307 |
| 5,339,796 A | * | 8/1994 | Manker | 126/263 B |
| 5,364,350 A | | 11/1994 | Dittman | 604/89 |
| 5,534,021 A | | 7/1996 | Dvoretzky et al. | |
| 5,580,573 A | | 12/1996 | Kydonieus et al. | 424/449 |
| 5,605,536 A | | 2/1997 | Sibalis | 604/20 |
| 5,626,571 A | | 5/1997 | Young et al. | 604/370 |
| 5,651,768 A | | 7/1997 | Sibalis | 604/20 |
| 5,658,583 A | | 8/1997 | Zhang et al. | 424/402 |
| 5,662,624 A | | 9/1997 | Sandstrom et al. | |
| 5,728,057 A | | 3/1998 | Ouellette et al. | 604/62 |
| 5,728,058 A | | 3/1998 | Ouellette et al. | 602/62 |
| 5,728,146 A | | 3/1998 | Burkett et al. | 607/109 |
| 5,733,255 A | | 3/1998 | Dinh et al. | 604/20 |
| 5,735,889 A | | 4/1998 | Burkett et al. | 607/96 |
| 5,741,318 A | | 4/1998 | Oullette et al. | 607/108 |
| 5,837,005 A | | 11/1998 | Viltro et al. | 607/112 |
| D403,778 S | | 1/1999 | Davis et al. | D24/206 |
| D403,779 S | | 1/1999 | Davis et al. | D24/206 |
| 5,860,945 A | | 1/1999 | Cramer et al. | 602/62 |
| D407,822 S | | 4/1999 | Davis et al. | D24/206 |
| D407,824 S | | 4/1999 | Davis et al. | D24/206 |
| D408,923 S | | 4/1999 | Davis et al. | D24/206 |
| D409,757 S | | 5/1999 | Davis et al. | D24/206 |
| 5,904,710 A | | 5/1999 | Davis et al. | 607/108 |
| 5,906,637 A | | 5/1999 | Davis et al. | 607/108 |
| 5,906,830 A | | 5/1999 | Farinas et al. | 424/448 |
| 5,919,479 A | | 7/1999 | Zhang et al. | |
| 5,925,072 A | | 7/1999 | Cramer et al. | 607/108 |
| D412,751 S | | 8/1999 | Davis et al. | D24/206 |
| 5,962,011 A | * | 10/1999 | De Villez et al. | 424/448 |
| D417,283 S | | 11/1999 | Davis et al. | D24/206 |
| 5,980,562 A | | 11/1999 | Ouellette et al. | 607/108 |
| 5,984,995 A | * | 11/1999 | White | 75/230 |
| D418,606 S | | 1/2000 | Davis et al. | D24/206 |
| 6,019,782 A | | 2/2000 | Davis et al. | 607/96 |
| 6,020,040 A | | 2/2000 | Cramer et al. | 428/64.1 |
| 6,024,761 A | | 2/2000 | Barone et al. | 607/108 |
| 6,042,673 A | | 3/2000 | Johnson et al. | 156/227 |
| 6,048,326 A | | 4/2000 | Davis et al. | 602/26 |
| 6,099,556 A | * | 8/2000 | Usui | 607/114 |

FOREIGN PATENT DOCUMENTS

| | | |
|---|---|---|
| WO | WO 97/01313 | 1/1997 |
| WO | WO 97/36968 | 10/1997 |
| WO | WO 97/49361 | 12/1997 |
| WO | WO 98/28021 | 7/1998 |
| WO | WO 98/28024 | 7/1998 |
| WO | WO 98/29063 | 7/1998 |
| WO | WO 98/29064 | 7/1998 |
| WO | WO 98/29065 | 7/1998 |
| WO | WO 98/29066 | 7/1998 |
| WO | WO 98/29067 | 7/1998 |
| WO | WO 99/09917 | 3/1999 |
| WO | WO 99/09918 | 3/1999 |

OTHER PUBLICATIONS

Knutson et al., "Solvent–Mediated Alterations of the Stratum Comeum," *Journal of Controlled Release*, vol. 11,(1990), pp.93–103.

Lycka, "EMLA, A New and Effective Topical Anesthetic," *J. Dermotol, Surg. Oncol.*, vol. 18, (1992), pp. 859–862.

McCafferty, et al., "New Patch Delivery System for Percutaneous Local Anaesthesia," *British Journal of Anaesthesia*, vol. 71, (1993) pp. 370–374.

Woolfson, *Percutaneous Local Anaesthesia*, E. Horwood, N.Y. (1993), pp. 166–170.

Astra USA, Inc., "EMLA Cream Product Information Form for American Hospital Formulary Service," (1993), pp. 1–28.

"Room Temperature," Macmillan, U.S.A., *Webster's New World College Dictionary*, Third Edition, 1997, p. 1165.

Florey, Klaus, *Analytical Profiles of Drug Substances*, vol. 15, 1986, pp. 150–231.

Florey,Klaus,*Analytical Profiles of Drug Substances*, vol. 12, 1983, pp. 73–105.

"Local Anesthetics, Parenteral, General Statement," *AHFS Drug Information*, 1992.

Florey,Klaus,*Analytical Profiles of Drug Substances*, vol. 18, 1989, pp. 379–411.

Sakamoto et al., "Dermal patch anaesthesia: comparison of 10% lignocaine gel with absorption promoter and EMLA cream," *Anesthesia*, (1993), vol. 48, pp. 390–392.

Dvoretzky, Israel, M.D., Hyperthermia Therapy for Warts Utilizing a Self–administered Exothermic Patch, *Dermal Surgery*, (1996), vol. 22, pp. 1035–1039.

Dvoretzky, Israel,M.D., Hyperthermia Therapy for Warts Utilizing a Self–administered Exothermic Patch, *Dermal Surgery*, (1996), vol. 22, pp. 1035–1039.

Stern, Peter, M.D. and Levine, Norman, M.D., "Controlled Localized Heat Therapy in Cutaneous Warts," *Arch. Dermatol*, (Jul. 1992), vol. 128, pp. 945–948.

* cited by examiner

METHOD FOR MANUFACTURING A HEAT GENERATING APPARATUS

BACKGROUND OF THE INVENTION

1. Field of the Invention

The current invention is related to novel designs and methods for manufacturing heating devices that generate heat by oxidation reaction.

2. Relevant Technology

Heating devices for heating human skin are plentiful in the art. The heating element used in a heating device has a significant impact on the design and overall performance of the heating device. As a heat generating medium, the use of elements capable of undergoing an exothermic oxidation reaction has the advantage of being controlled by exposing the oxidation reaction elements to ambient oxygen. For example, an oxidation-based, heat-generating hand warmer may comprise an air-permeable bag containing a heat generating medium. The mixture may comprise loose granules of iron powder, activated carbon, water, salt, and optionally a material such as wood powder for making the medium more porous. The hand warmer is usually stored in an airtight container. After it is taken out of the container, oxygen in ambient air flows into the heat generating medium through the air-permeable bag, and the exothermic oxidation of iron powder in the heat generating medium starts to generate heat.

With apparatus designed for warming the hand or body, the heating devices are not usually manufactured to be compact, and the heating temperature and duration of heat generated are not designed to be precisely controlled. For example, the hand warmer distributed by GRABBER Warmers, Grand Rapids, Mich. 49512 has minimum and maximum temperatures of 40° C. and 69° C., respectively, and weighs about 20 grams. However, in some situations the size of the heating device and the ability to control temperature and duration of the heat may be important.

U.S. Pat. No. 5,658,583 discloses oxidation-reaction based devices to generate heat for enhancing dermal drug delivery. A heat generating device as disclosed in the patent is a thin, flexible chamber defined by a bottom and surrounding walls made of materials non-permeable to air, and a cover with a structure which allows oxygen in ambient air to flow into the chamber at a proper rate. Inside the thin, flexible chamber is a heat generating medium capable of generating heat when exposed to oxygen. A typical composition of the heat generating medium include activated carbon, iron powder, sodium chloride, fine wood powder, and water in a proper ratio.

In many medical related applications, such as enhancing transdermal drug delivery and regulating injected or implanted controlled drug release systems, the heating device must meet certain criteria for the device to be functional and practical. For example, the device usually needs to be thin and compact. The duration and temperature of the heat generated need to be precisely controlled and reproducible, so that the risk of drug overdose or under dose can be minimized. Additionally it is often desirable to be able to place as much heat generating medium into the chamber as possible, so that the heating device, while compact, can generate heat for sufficient duration. Moreover, the device may need to be sterile and disposable. The design and manufacturing process of the heat generating medium affects the potential applications of the heating device.

The task of designing and efficiently manufacturing heating elements in a heating device can be difficult. For example, one way to place the heat generating medium into a device is to pre-mix all of the ingredients of the heat generating medium together, and then load the pre-mixed heat generating medium into the chamber or a bag. Manufactured in this way, the heat generating medium is in the form of loose granules or coarse powder. The chamber or the bag is then closed and sealed into an air-tight container. However, the difficulties associated with directly loading pre-mixed heat generating medium into a chamber or bag make such an approach undesirable in some situations.

One drawback of the method described above is that, the pre-mixed granules or coarse powder are usually loose so that the quantity of the pre-mixed heat generating medium that can be loaded into a unit volume is not maximized. Additionally, the particles in the pre-mixed granules are often attracted by electric static and fly outside the chamber during loading. Furthermore, the pre-mixed heat generating medium starts to generate heat immediately upon contacting oxygen and starts losing its ability to generate heat later on. To prevent the exothermic reaction from occurring prematurely in such a process, the components need to be mixed, transported, and loaded into the chamber in an oxygen free environment. An oxygen-free environment can be expensive to create and maintain.

These limitations in design and manufacturing can pose serious problems for certain applications, such as in many medically related applications, and when the volume of the chamber is designed to be small. Thus, it would be advantageous to develop a better method for manufacturing oxidation-based heating devices.

OBJECTS AND BRIEF SUMMARY OF THE INVENTION

In view of the foregoing, it is an object of at least one embodiment of the present invention to increase the amount of heat generating medium per unit volume in a heat generating device.

It is also an object of at least one embodiment of the present invention to provide a more homogenous uniform distribution of heat generating medium in the heating device.

It is another object of at least one embodiment of the present invention to inhibit oxidation of the heat generating medium during the manufacturing process.

It is an additional object of at least one embodiment of the present invention to allow the manufacturing process to be done in normal ambient air.

It is further an object of at least one embodiment of the present invention to ensure that the final water percentage (water ratio) in the heat generating medium of the heating device is as close to the ideal water percentage for the oxidation reaction as is possible.

It is yet another object of the present invention to provide a manufacturing process for making controlled heating devices that use oxidation reactions to generate heat which are suitable for use in medical and therapeutic-related uses.

The current invention is related to novel designs and methods for manufacturing heating devices that generate heat by oxidation reaction.

The limitations discussed have not been successfully addressed in the art until now and thus, prior art devices do not operate with precise heating, duration and temperature and/or are not compact.

Manufacturing approaches addressed in the present invention relate to, first, the difficulty in manufacturing the heat generating medium which is activated by oxygen present in the atmosphere, and second, the difficulty in loading the generating medium into the heating device in such a way as to maximize the amount of medium per unit volume in the device and provide for uniform heating. To reduce the loss of heat generating potential due to untimely reaction of the heat generating medium with ambient oxygen during the manufacturing process, the present invention provides means for inhibiting oxidation in a heat generating medium during the manufacturing process. At an appropriate time during the manufacturing process, the oxidation capacity of the heat generating medium is substantially restored. To address the difficulties involved with loading the heat generating medium into the heating device, the present invention provides a loading facilitator to increase the amount of heat generating medium per volume dispersed within the heating device and to provide an even and uniform distribution of the heat generating medium. When appropriate, the loading facilitator is removed from the heat generating medium within the device. The description below explains in greater detail the aspects of the present invention.

In a typical oxidation-reaction-based heat generating medium, the ratio of water in the medium is critical to the heat generating function. For example, when using a mixture of iron powder, activated carbon, sodium chloride, wood powder and water, if the water ratio is too high relative to the other components, the oxidation reaction either will not take place or will be at such low rates that proper heat cannot be generated. Similarly, if the ratio of water is too low, the reaction will not take place or will not generate the necessary heat. The present invention utilizes the water ratio requirements of oxidation reactions in a novel way that makes the manufacturing of oxidation-based heat generating devices easier, and allows manufacturing to take place in ambient air without losing significant heat generating capacity of the products. Using this method, heating devices which have more precisely controlled heating temperature and duration can be manufactured. In addition, this method also allows precise loading of small quantities of heat generating medium, (e.g., less than 1.0 grams) into very thin and shallow heating device chambers.

In this application, the terms "oxidation-facilitator" and "oxidation facilitating substance" are defined as a substance, the existence of which is necessary for the heat generating medium to generate heat properly upon contact with oxygen. The terms "oxidation-inhibitor" and "oxidation inhibiting substance are defined as a substances which, if added into an oxidation based heat generating medium significantly inhibits the heat generating capacity of the heat generating medium. Some embodiments of the present invention will employ an oxidation inhibitor rather than an oxidation facilitator. The inhibitor or facilitator can be a single substance, a mixture of substances, or a solution. In one embodiment the facilitator and inhibitor exist in a liquid state at manufacturing and/or application temperature and are therefore referred to as an "oxidation facilitating liquid" and an "oxidation inhibiting liquid," respectfully.

BRIEF DESCRIPTION OF THE ILLUSTRATIONS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
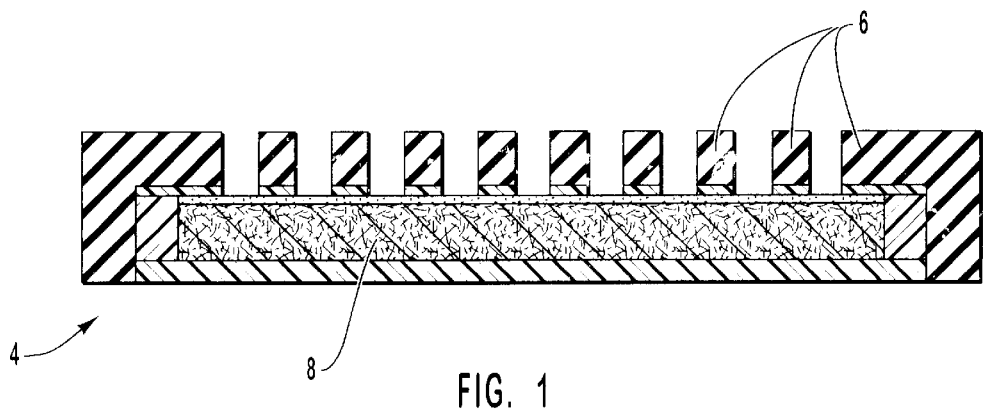
FIG. 1 shows a cross section of one embodiment of a heat generating device with thermal insulation.
Figure 2:
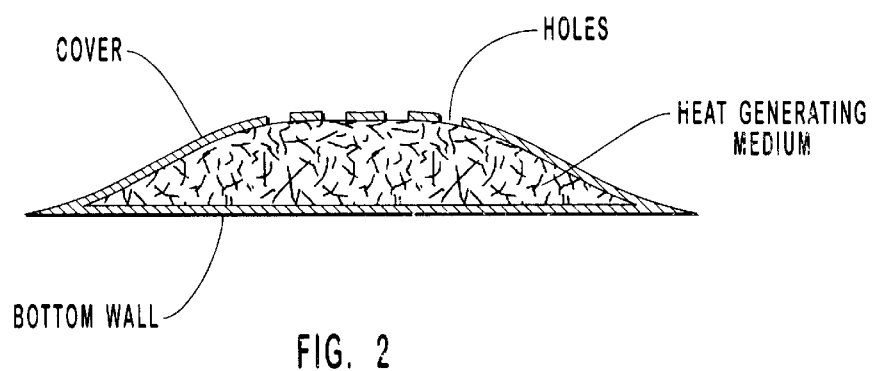
FIG. 2 shows a cross section of one embodiment of a heat generating device.

The foregoing and other objects and features of the present invention will become more fully apparent from the following description and appended claims.

In one method of this invention, all of the ingredients of a heat generating medium except water (i.e. activated carbon, iron powder, wood powder, sodium chloride in a proper ratio) are mixed with a volatile, oxidation inhibitor (e.g. alcohol) to form granules or, preferably in many cases, a slushy substance. The actual form of the mixture depends on the amount of the oxidation-inhibiting liquid added. If the amount is small relative to other ingredients, granules may be formed. When the amount is large enough, a slushy substance can be formed. Excess amounts of the oxidation-inhibiting liquid can make the viscosity of the slush too low, which may cause iron powder to precipitate to the bottom. This should be avoided. The slush or the granules are then loaded into a container, such as a chamber or a bag.

In the next step, the oxidation-inhibiting liquid is then removed. The oxidation-inhibiting liquid may be removed by evaporation or other methods, such as centrifugation, depending on the structure of the container and other considerations. In the process of evaporating the oxidation-inhibiting liquid, some small amount of heat might be generated because moisture in air may facilitate oxidation. Although this heat generation is usually minimal and insignificant, ideally it should be minimized by means such as using minimal evaporation time and dry and/or hot evaporation environment. All of the above processes can be performed in normal ambient air, since the oxidation reaction cannot take place at significant rates in the absence of an oxidation-facilitating liquid, such as water.

After the oxidation-inhibiting liquid is substantially evaporated, a desired amount of water is quickly dropped onto the surface of the now modified, "dried," heat generating medium and the container is closed. If the container is a chamber, the chamber is capped with a cover that has desired air-permeability. The entire heating device is then sealed into an air-tight container or pouch. During the time between when the water is dropped into the heat generating medium and the device is sealed into the air-tight container or pouch, only a small amount of the heat generating medium is subject to oxidation reaction. That is because immediately after being dropped into the waterless heat generating medium, water is not homogeneously distributed in the medium. In the place(s) where water is dropped, there is too much water for the oxidation reaction to take place at full rate or efficiently. In places far from the site where water is dropped, there is not enough water to start the oxidation reaction at full rate or efficiently. This gives time to apply the cover of the chamber and seal the device into the air-tight container without significant loss of the heat generating capacity.

In situations that require even less loss of the heat generating capacity, a pre-determined amount of ice, instead of water, can be added into the "dried," waterless heat generating medium before placing the cover and sealing the device into the air-tight container. Optionally, oxygen may be removed from the air-tight container before sealing by methods such as vacuuming or nitrogen purging. However, in many cases the removal of oxygen is not necessary, since after sealing the heat generating device into the container, the limited amount of oxygen sealed in the container will be used up in the reaction with the heat generating medium before significantly reducing the heat generating potential. This process may cause some loss of the heat generating capacity of the heat generating medium, but the loss is usually minimal and finite, and in most cases does not affect the function of the device significantly. More importantly, much is gained by foregoing the removal of oxygen. Because the present invention allows the entire process to be conducted in normal ambient air instead of an oxygen-free environment, the cost and complexity of manufacturing can be reduced.

After the device is completely sealed, water continues to diffuse into the entire body of the heat generating medium, and eventually reaches a homogeneous distribution. In the cases where ice instead of water is added, the ice will first melt into water, which will eventually reach a homogeneous distribution. The amount of time it takes to reach even distribution will depend on the amount of heat generating medium. Since the total amount of water added into the heat generating medium is predetermined to allow proper heat generation, every part of the heat generating medium is ready to generate heat properly upon contact with oxygen after homogeneous water distribution is reached.

A proper mixture of iron powder, activated carbon, wood powder and water (i.e. a weight ratio of about 5:16:3:6) can generate heat at certain rates upon contact with oxygen, but the addition of substances such as sodium chloride, potassium chloride, and magnesium chloride can increase the heat generation rates. In the discussion above, the salt (sodium chloride) was added in the waterless powder mixture before mixing with the inhibitor. As an alternative method, iron powder, activated carbon and wood powder may be mixed with the inhibitor without mixing in water or sodium chloride. After the removal of the inhibitor, the proper amount of salt-in-water solution can be added into the "dried" heat generating medium before sealing the device into the air-tight container.

Another advantage of one embodiment of the present invention is that it allows packing more heat generating medium into a unit volume than directly loading completely pre-mixed heat generating medium, which is usually in the form of a loose granules. A higher heat generating medium per unit volume ratio allows for a more compact, and relatively longer lasting heating device. Moreover, loading the heat generating medium into the heat generating chamber according to one embodiment of the present invention provides for a more intimate contact with the bottom wall of the chamber than would be possible with loose granules. The loading technique of the present invention will facilitate the efficient transfer of heat generated in the heat generating medium to the drug delivery system or tissue under the heating patch through the bottom wall of the chamber.

This manufacturing method advantageously allows the heat generating medium to be cast into the chamber, so that the heat generating medium can be made to evenly distribute over the entire area of the chamber. With one embodiment, this is easily accomplished by gentle tapping or shaking. To spread a heat generating medium in the form of loose granules evenly over the entire area of the chamber can be difficult and awkward. One has to spread and reposition the loose granule(s) with a spreading toot or similar object. This requires considerably more care than the techniques of the present invention. Also, in an embodiment of this method, the only volatile substance in the final mixture of heat generating medium, namely water, is added in the last step and shortly before the entire device is sealed into the air-tight bag. This ensures that the final water percentage (water ratio) in the heat generating medium remains as close to the ideal water percentage as possible.

Pre-mixing the substances used for the heat generating element all together and then loading them into the device can be inefficient in some circumstances and impractical in others. Water can evaporate in the process which may lead to an insufficient final water percentage in the heat generating medium. Insufficient water may in turn lead to heat durations and/or temperatures that are different than designed. In the context of heat aided drug delivery this can alter the delivered drug dosage, with serious consequences for the patient.

In an alternative method of the invention, all of the components of a heat generating medium except water (i.e. activated carbon, iron powder, wood powder, sodium chloride in a proper ratio) are mixed thoroughly and loaded into a chamber. The proper amount of water is then added into the chamber. A cover is then applied to the chamber before the chamber is placed into an air-tight container. As in the previously described method, uneven water distribution immediately after the addition of water prevents the medium from reacting completely or efficiently. Because the medium cannot effectively react, the cover to the chamber can be applied in a regular, ambient environment with minimal loss of heat generating capacity of the medium.

In another alternative method, predetermined amounts of activated carbon, iron powder and wood powder are mixed with an excess amount of water to obtain a slush. For example, the weight ratio of activated carbon, iron powder, wood powder and water is 5:16:3:20. The amount of water added exceeds the appropriate amount for a proper oxidation reaction, such that heat generation by the slushy matter is severely inhibited, even when exposed to oxygen. A predetermined amount of the slush can then be loaded into an open chamber. The device is then placed into an oxygen-free environment for removing the water, such as by evaporation. After substantially all of the water is removed, a predetermined amount of a sodium chloride in water solution is added to the medium in the open chamber. The amount of water in the sodium chloride water solution added to the medium in combination with any residual water in the medium is adequate to allow the medium to generate heat at desired rates upon exposure to oxygen. The medium will be capable of generating heat after the water is substantially distributed.

This method requires an oxygen-free environment during removal of the inhibitor, however it has some advantages. The advantages of this method include: 1) allowing the mixing of the substances to be done in normal, ambient air; 2) allowing the transfer of the slush from air into the oxygen-free environment without losing heat generating capacity; 3) providing a convenient way to add a precise amount of water into the medium; and 4) combining the dual benefits of water as both an oxidation inhibitor and as a necessary ingredient in the heat generating medium, may mean lower manufacturing costs, greater safety, or less pollution to the environment.

The methods described here provide specific advantages for making heating devices used in medical related applications. They also provide advantages for making heating devices for other applications, such as warming the hand or body. That is because even in non-medical applications it may be desirable to have precise control of heating duration and temperature, to have a heating device of compact size, and to have easier and lower cost manufacturing than other methods provide.

Another novel feature of this invention is providing thermal insulation to the heat generating devices. As shown in FIG. 1, one embodiment of the present invention insulates the heat generating medium from ambient air in all directions except the surface used for passing the heat to the object being heated (i.e. a transdermal drug patch, a skin area under the heating device). Thermal insulation 6 around the heat generating medium 8 in the device 4 helps to isolate the device 6 from the outside environment and allows better heat accumulation in the heat generating medium 8. That means, compared with a device without such thermal insulation, the same heating temperature can be achieved with lower heat generation rate. The present invention allows a given amount of heat generating medium to last longer, which is very desirable for devices that need to be compact. This may also minimize the potential for risk of burning the skin if the heating device is directly applied on the skin by allowing the heat generating medium to be effective while generating a slightly lower heat temperature.

The present invention also insulates the heat generating medium to minimize the influence of the outside environment on the temperature of the object being heated. This allows more precise temperature control at the object, which may be very important in medical related applications and some other application. For instance, use of the present invention may minimize the potential for drug overdose or under dose if the heating device is used to enhance drug absorption from a dermal drug patch.

EXAMPLE 1
(Actual)

An actual heating patch was manufactured with a method described above. The steps of the process are explained below.

Step 1. Selecting An Open Chamber and Cover

An open chamber and cover suitable for medical applications were selected. The open chamber was defined by a surrounding wall and a bottom wall. The rectangular ring-shaped surrounding wall was made of a closed-cell foam tape(3M 1779), and had inner dimensions of about 1.0 inches by 1.625 inches and outer dimensions of about 1.5 inch by 2.125 inch, with 0.125 inch rounded corners. The height of the surrounding wall was $\frac{1}{16}$ inch. The rectangular bottom wall was made of a thin plastic tape (3M 1525L), and had the dimensions corresponding to the outer dimensions of the surrounding wall. The bottom side of the bottom wall is adhesive. The bottom side is covered by a protective liner prior to application. The surrounding wall was adhered onto the bottom wall to form an open, shallow chamber.

The cover of the chamber was a rectangular closed-cell foam tape (3M 9773) with 8 holes (diameter about $\frac{1}{16}$ inch). The thickness of the foam tape was about $\frac{1}{32}$ inch. The two dimensions of the cover corresponded to the outer dimensions of the bottom wall. The holes were covered with a microporous membrane (3MCoTran 9711).

Step 2. Mixing All of the Ingredients of the Heat Generating Medium, Except Water with An Oxidation-Inhibitor Activated carbon (Norit Americas Inc, Grade HDC), iron powder (SCM Metal Products, Inc. Grade A131), fine wood powder and sodium chloride in the weight ratio of about 5:16:3:2 were mixed together thoroughly to obtain a powder mixture. About fifty-five weight portions of pure ethyl alcohol were then added into every 100 weight portions of the mixed powder. The powder mixture and alcohol were stirred thoroughly to obtain a slushy matter mixture. The selected "alcohol to mixed powder ratio" yielded a slushy matter that was fluid enough to be cast into the thin open chamber of Step 1, but that was also thick enough so that the iron powder in the slushy matter did not easily precipitate in the liquid and settle to the bottom of the slushy matter.

Step 3. Loading the Slushy Matter and Evaporating the Alcohol

About two grams of the modified heat generating medium, the slushy matter, was placed into each open chamber made in Step 1 and was spread to cover most of the bottom area of the open chamber. The chamber was gently shaken to make the slushy matter to evenly cover the entire bottom of the chamber. The alcohol was removed from the slushy matter by placing the loaded chamber in a hood for about two hours to evaporate the alcohol. After two hours, the matter was dry, but slight alcohol odor could still be detected, suggesting most of the alcohol was evaporated but there was still residual amount of alcohol in the remaining mixture. The heat generating medium evenly covered the entire bottom of the chamber.

Step 4. Adding Water and Sealing Into Air-Tight Pouch

After the alcohol in the chamber was evaporated, about 0.3 mL water was added to the mixture to eventually form the appropriate heat generating mixture or medium (after homogeneous distribution of water is reached). The cover made in Step 1 was adhered onto the open chamber to form a closed chamber inside which the heat generating medium resided. The entire device was then placed into a pouch made of an air-tight film (Perfecseal 35785G). The opening of the pouch was then sealed by heat, so that the heating device was isolated from the outside environment.

Step 5. Allowing Water To Diffuse in Order To Be Evenly Distributed

After the device was sealed in the pouch, the water was allowed to diffuse throughout the heat generating medium. The water eventually reached homogenous distribution, allowing the patches to function efficiently. In this example, the entire manufacturing process was performed in normal ambient air. Patches made with the above method were tested on human skin a few days after they were made. The patch was removed from the air-tight pouch, the protective liner was removed and the patch was adhered on the skin of the human subject, using the adhesive bottom of the chamber. A thin temperature probe was placed between the bottom of the heating patch and the subject's skin to monitor the temperature. Table A shows the temperature produced by two of the patches, as measured by the temperature probe, as a function of time. Table B shows the temperature produced by another similar patch, measured for a longer period of time.

TABLE A

| Time (min) | Patch #1 | Patch #2 |
|---|---|---|
| 0 | 23.5 | 23.2 |
| 1 | 28.3 | 30.9 |
| 2 | 31.8 | 33 |
| 3 | 33.4 | 34.7 |
| 4 | 34.4 | 36.1 |
| 5 | 36.4 | 37.8 |
| 6 | 37.2 | 38.2 |
| 7 | 37.9 | 38.5 |
| 8 | 37.9 | 38.7 |
| 9 | 38 | 39.2 |

TABLE A-continued

| Time (min) | Patch #1 | Patch #2 |
|---|---|---|
| 10 | 38.2 | 39.7 |
| 11 | 38.2 | 39.7 |
| 12 | 38.9 | 39.7 |
| 13 | 38.7 | 39.7 |
| 14 | 38.6 | 39.9 |
| 15 | 38.8 | 40 |
| 16 | 38.8 | 40.1 |
| 17 | 38.9 | 40.1 |
| 18 | 38.9 | 40.2 |
| 19 | 39 | 40.2 |
| 20 | 39 | 40.2 |
| 21 | 39.1 | 40.3 |
| 22 | 38.9 | 40.4 |
| 23 | 38.8 | 39.3 |
| 24 | 38.9 | 40.5 |
| 25 | 38.9 | 40.5 |
| 26 | 38.9 | 40.4 |
| 27 | 38.8 | 40.4 |
| 28 | 38.8 | 40.4 |
| 29 | 38.9 | 40.3 |
| 30 | 38.9 | 40.3 |
| 31 | 38.8 | 40.2 |
| 32 | 38.9 | 40.1 |
| 33 | 38.7 | 40.1 |
| 34 | 38.7 | |
| 35 | 38.6 | |

TABLE B

| Time (min) | Patch #3 |
|---|---|
| 0 | 30.5 |
| 1 | 32.7 |
| 2 | 34.1 |
| 3 | 35.6 |
| 4 | 36.6 |
| 5 | 37.1 |
| 6 | 37.8 |
| 7 | 38.2 |
| 8 | 38.5 |
| 9 | 38.6 |
| 10 | 38.6 |
| 11 | 38.9 |
| 12 | 38.9 |
| 13 | 38.9 |
| 14 | 39 |
| 15 | 39.1 |
| 20 | 39.2 |
| 25 | 39.5 |
| 30 | 39.7 |
| 35 | 39.6 |
| 40 | 39.5 |
| 45 | 39.3 |
| 50 | 39.3 |
| 55 | 39.2 |
| 60 | 39.3 |
| 65 | 39.3 |
| 70 | 39.5 |
| 75 | 39.1 |
| 80 | 39.3 |
| 85 | 39.5 |
| 90 | 39.3 |
| 95 | 39 |
| 100 | 39.1 |
| 105 | 39.2 |
| 110 | 39.1 |
| 115 | 39.5 |
| 120 | 39.4 |
| 125 | 39.3 |
| 130 | 39 |
| 135 | 38.8 |
| 140 | 38.5 |
| 145 | 38.1 |
| 150 | 37.7 |
| 155 | 37 |
| 160 | 36.6 |
| 165 | 36.4 |
| 170 | 36.1 |
| 175 | 36 |
| 180 | 35.8 |
| 185 | 35.8 |
| 190 | 35.7 |
| 195 | 35.7 |
| 200 | 35.6 |
| 205 | 35.6 |
| 210 | 35.6 |
| 215 | 35.3 |
| 220 | 35.2 |
| 225 | 35.2 |
| 230 | 35.1 |
| 235 | 35.1 |
| 240 | 35.1 |
| 245 | 34.9 |
| 250 | 34.9 |

The amount of each component, especially water, of the heat generating medium in the chamber was precisely controlled. The skin area heated by the heating patch was about 10 cm2. Although the heating patch only had about 1.6 g heat generating medium in it, the temperature of the skin was rapidly raised into a narrow, elevated range. The data in Table B show that the temperature was maintained in the narrow, elevated range for more than 2 hours before decreasing gradually.

In the device of this example, the heat generating medium was contained in a thin, shallow chamber. The cover and the surrounding wall of the chamber were made of materials with thermal insulating properties (foam tape), but the bottom was made of a thin, plastic tape with minimal thermal insulating property. Therefore, heat was effectively passed from the heat generating medium to the object in contact with the bottom of the chamber, but heat loss via the surrounding wall and the cover was minimized. In addition, influence from the ambient air on the skin under the heat patch was minimized.

In another actual experiment testing the heat generating device, a heat generating device comprised side walls defined by a ¼ inch thick rectangular foam tape (4 layers of No. 1779 1/16" white foam tape, 3M Corporation, Minneapolis, Minn., USA Corporation, Minneapolis, Minn., USA) with an outer dimension of about 2.25 inches by 4 inches with an opening therein inner dimension of about 1.75 by 3.5 inches, the bottom wall comprising rectangular medical tape (No. 1525L plastic medical tape, 3M Corporation, Minneapolis, Minn., USA Corporation, Minneapolis, Minn., USA) of a dimension of about 2.25 inches by 4 inches with a non-adhesive side attached to the bottom of the side walls, and a top wall comprising a rectangular 1/32 inch thick foam tape (No. 9773 1/32" tan foam tape, 3M Corporation, Minneapolis, Minn., USA Corporation, Minneapolis, Minn., USA) with thirty-two holes there through (diameters approximately 1/16 inch). The side walls, the bottom wall, and the top wall defined a chamber. The holes of the top wall were covered by an air permeable membrane comprising a microporous membrane (no. 9711 CoTran™ membrane, 3M Corporation, Minneapolis, Minn., USA Corporation, Minneapolis, Minn., USA) disposed between the top wall and the heat generating medium disposed in the chamber comprised a mixture of activated carbon, iron powder, saw dust, sodium chloride and water in the weight ratio of approximately 5:21:3:2:6 weighing approximately 31 grams.

This heating device was tested on a volunteer's skin with a temperature probe placed between the heating device and the volunteer's skin to measure the temperature. The results of this temperature experiment are illustrated in Table C, which shows that the heating device was capable of keeping the skin temperature to a narrow, elevated range between about 41 and 44° C. for extended periods of time (at least 840 minutes).

TABLE C

| Time (minutes) | Temperature (° C.) |
|---|---|
| 0 | 31.9 |
| 1 | 32.2 |
| 2 | |
| 3 | 33.2 |
| 4 | 33.8 |
| 5 | 34.4 |
| 6 | 34.8 |
| 7 | 35.8 |
| 8 | 35.9 |
| 9 | 36.7 |
| 10 | 37.3 |
| 11 | 37.8 |
| 12 | 38.4 |
| 13 | 38.7 |
| 14 | 39.2 |
| 15 | 39.4 |
| 16 | 39.8 |
| 17 | 39.9 |
| 18 | 40.1 |
| 19 | 40.3 |
| 20 | 40.5 |
| 22 | 40.8 |
| 24 | 40.9 |
| 26 | 41 |
| 28 | 41.1 |
| 30 | 41.1 |
| 35 | 41 |
| 40 | 41 |
| 45 | 40.9 |
| 75 | 41.1 |
| 150 | 41.7 |
| 210 | 41.6 |
| 300 | 41.5 |
| 390 | 41.7 |
| 510 | 41.4 |
| 570 | 41.5 |
| 720 | 41.4 |
| 780 | 41.4 |
| 840 | 41.5 |

EXAMPLE 2

In another example, all the ingredients of the heat generating medium, except is water, are mixed to form a mixed powder. The mixed powder is then loaded directly into the open chamber as in Example 1. More specific details of the process are set forth below.

Step 1. The Open Chamber and the Cover

The open chamber is defined by a surrounding wall and a bottom wall. The rectangular ring-shaped surrounding wall is made of a closed-cell foam tape, and has inner dimensions of about 1.0 inches by 1.625 inches and outer dimensions of about 1.5 inch by 2.125 inch, with 0.125 inch rounded corners. The height of the surrounding wall is ⅛ inch. The rectangular bottom wall is made of a thin plastic tape and has dimensions corresponding to the outer dimensions of the surrounding wall. The surrounding wall is adhered onto the bottom wall to form a open shallow chamber. The cover of the chamber is an rectangular closed-cell foam tape with 8 holes (diameter about 1/16 inch). The dimensions of the cover correspond to these of the bottom wall. The holes are covered with a microporous membrane.

Step 2. Mixing All Ingredients of the Heat Generating Medium, Except Water

Activated carbon, iron powder, fine wood powder and sodium chloride in the weight ratio of about 5:16:3:2 are mixed together thoroughly. This forms the waterless, intermediate heat generating medium, which is in the form of a powder mixture.

Step 3. Loading the Waterless, Intermediate Heat Generating Medium

About 1.3 g of the waterless heat generating medium of Step 2 is placed in the open chamber of Step 1. The powder is spread evenly to cover the entire bottom of the chamber.

Step 4. Adding Water and Isolating

About 0.3 mL water is placed into the waterless heat generating medium. The cover of Step 1 is adhered onto the chamber so the heat generating medium is completely enclosed in the chamber. The entire device is then heat sealed into an air-tight pouch.

EXAMPLE 3

In another example, a manufacturing process similar to that in Example 1 is employed, except that in Step 2, the mixed powder has no sodium chloride but only activated carbon, iron powder, and wood powder in the weight ratio of about 5:16:3. Also, the proper amount of sodium chloride is dissolved in the water, and the sodium chloride in water solution, instead of water, is added into the dried, heat generating medium in Step 4. The steps of Example 1 with these variations are explained below.

Step 1. Selecting An Open Chamber and Cover

An open chamber and cover suitable for medical applications are selected. The open chamber is defined by a surrounding wall and a bottom wall. The rectangular ring-shaped surrounding wall is made of a closed-cell foam tape(3M1779), and has inner dimensions of about 1.0 inches by 1.625 inches and outer dimensions of about 1.5 inch by 2.125 inch, with 0.125 inch rounded corners. The height of the surrounding wall is 1/16 inch. The rectangular bottom wall is made of a thin plastic tape (3M1525L), and has the dimensions corresponding to the outer dimensions of the surrounding wall. The surrounding wall is adhered onto the bottom wall to form an open, shallow chamber.

The cover of the chamber is a rectangular closed-cell foam tape (3M 9773) with 8 holes (diameter about 1/16 inch). The thickness of the foam tape is about 1/32 inch. The two dimensions of the cover corresponds to the outer dimensions of the bottom wall. The holes are covered with a microporous membrane (3MCoTran 9711).

Step 2. Mixing Ingredients of the Heat Generating Medium, Except Sodium Chloride and Water with An Oxidation-Inhibitor Activated carbon (Norit Americas Inc, Grade HDC), iron powder (SCM Metal Products, Inc. Grade A131), and fine wood powder in the weight ratio of about 5:16:3 are mixed together thoroughly to obtain a mixed powder. About fifty-five weight portions of pure ethyl alcohol are then added into every 100 weight portions of the mixed powder. The mixture is stirred thoroughly to obtain a slushy matter. The selected "alcohol to mixed powder ratio" yields a slushy matter that is fluid enough to be cast into the thin open chamber of Step 1, but that is also thick enough so that the iron powder in the slushy matter does not easily precipitate in the liquid and settle to the bottom of the slushy matter.

Step 3. Loading the Slushy Matter and Removing the Alcohol

About two grams of the slushy matter is placed into each open chamber made in Step 1 and is spread to cover most of the bottom area of the open chamber. The chamber is gently shaken to make the slushy matter to evenly cover the entire bottom of the chamber. The alcohol is removed from the slushy matter by placing the loaded chamber in a hood for about two hours to evaporate the alcohol. After two hours, the matter is dry, but slight alcohol odor may be detected, suggesting most of the alcohol is evaporated but there is still residual amount of alcohol in the matter. The heat generating medium evenly covers the entire bottom of the chamber.

Step 4. Adding Sodium Chloride and Water and Sealing Into Air-Tight Pouch

After the alcohol in the chamber is evaporated, about 0.4 g water with sodium chloride dissolved therein [about 1 weight portion of sodium chloride dissolved in 3 wight portions of water] is placed into the heat generating medium. The amount of sodium chloride dissolved in the water is sufficient to replace the sodium chloride left out of the dry mix formulation which in dry mix has a weight ratio of 2 parts. The cover made in Step 1 is adhered onto the open chamber to form a closed chamber inside which the heat generating medium resided. The entire device is then placed into a pouch made of an air-tight film (Perfecseal 35785G). The opening of the pouch is then sealed by heat, so that the heating device is isolated from the outside environment.

Step 5. Allowing Water To Diffuse in Order To Be Evenly Distributed

After the device is sealed in the pouch, the water and sodium chloride are allowed to diffuse throughout the heat generating medium. The water with dissolved sodium chloride eventually reaches homogenous distribution, allowing the patches to function efficiently. In this example, the entire manufacturing process was performed in normal ambient air.

EXAMPLE 4
(Hypothetical)

In another example, a manufacturing process similar to that in Example 2 is employed, except that in Step 2, the mixed powder has no sodium chloride but only activated carbon, iron powder and wood powder in the weight ratio of about 5:16:3; and the proper amount of sodium chloride is dissolved in the water, and the sodium chloride in water solution, instead of water, is added into the dried, heat generating medium in Step 4. The steps of Example 2 with these variations are explained below.

Step 1. The Open Chamber and the Cover

The open chamber is defined by a surrounding wall and a bottom wall. The rectangular ring-shaped surrounding wall is made of a closed-cell foam tape, and has inner dimensions of about 1.0 inches by 1.625 inches and outer dimensions of about 1.5 inch by 2.125 inch, with 0.125 inch rounded corners. The height of the surrounding wall is ⅛ inch. The rectangular bottom wall is made of a thin plastic tape and has dimensions corresponding to the outer dimensions of the surrounding wall. The surrounding wall is adhered onto the bottom wall to form a open shallow chamber. The cover of the chamber is a rectangular closed-cell foam tape with 8 holes (diameter about 1/16 inch). The dimensions of the cover correspond to those of the bottom wall. The holes are covered with a microporous membrane.

Step 2. Mixing All Ingredients of the Heat Generating Medium, Except Water and Sodium Chloride Activated carbon, iron powder, and fine wood powder in the weight ratio of about 5:16:3 are mixed together thoroughly. This forms the waterless heat generating medium, which is in the form of a powder.

Step 3. Loading the Waterless Heat Generating Medium

About 1.3 g of the waterless heat generating medium of Step 2 is placed in the open chamber of Step 1. The powder is spread evenly to cover the entire bottom of the chamber.

Step 4. Adding Water and Isolating

About 0.3 mL water and sodium chloride is placed into the waterless heat generating medium. The amount of sodium chloride dissolved in the water is sufficient to allow efficient oxidation in the heat generating medium. The cover of Step 1 is adhered onto the chamber so the heat generating medium is completely enclosed in the chamber. The entire device is then heat sealed into an air-tight pouch.

Having thus described in detail preferred embodiments of the present invention, it is to be understood that the invention defined by the appended claims is not to be limited by particular details set forth in the above description as many apparent variations thereof are possible without departing from the spirit or scope thereof.

EXAMPLE 5

In another alternative method, a predetermined amount of activated carbon, iron powder, wood powder, sodium chloride, and an excessive amount of water are mixed together to obtain a slush. For example, the weight ratio of activated carbon, iron powder, wood powder, sodium chloride and water is 5:16:3:2:20. The amount of water added exceeds the appropriate amount for proper heat generation, so that heat generation by the slushy matter is severely inhibited even when exposed to oxygen. A predetermined amount of the slush can then be loaded into an open container or chamber. The device is then placed into an oxygen-free environment where water is then removed by evaporation. When the amount of water is removed such that the remaining amount of water is adequate for heat generation, the open container is closed or is capped with a cover with selected air permeability to form a closed container with selected air-permeability. The closed container is then sealed into an airtight container.

EXAMPLE 6

In another alternative method, a process similar to that in Example 5 is used, except that the excess amount of water is not removed by evaporation. Instead, a predetermined amount of a water absorbent material, such as activated carbon granules, is added into the medium to absorb the excess amount of water, so that the amount of water remaining in the medium is appropriate for heat generation.

EXAMPLE 7

In another alternative method, a predetermined amount of activated carbon, iron powder, wood powder, and sodium chloride are mixed together to form a powder mixture. For example, the weight ratio of activated carbon, iron powder, wood powder, and sodium chloride is 5:16:3:2. The mixed powder is loaded into a thin bag made of a porous material (i.e. filter paper, cloth, and paper). The thin bag (similar to a tea bag) is then closed. Predetermined amount of water or a salt solution is added onto the thin bag, and is absorbed into the powder mixture. The water eventually reaches a homogeneous distribution in the powder mixture to yield a heat generating medium. Immediately after water is added into the thin bag. The closed thin bag is placed into a chamber made of air-impermeable materials and a structure with selected air permeability (i.e. similar to the device in Example 1). The chamber is sealed into an air-tight pouch for storage. In this method, the thin bag containing the mixed powder can be easily made in mass quantities by automated equipment. The loading process is thus simplified.

EXAMPLE 8

In this example, the heat generating device has a bottom wall made of a material impermeable to air, and a curved cover made of a material impermeable to air. The curved cover has selected number of holes with selected size(s). The curved cover is curved such that its edge can be sealed onto the bottom wall (by heat or adhesive) to form a space between the bottom wall and the curved cover inside which a predetermined quantity of heat generating medium can be disposed. This device does not have a surrounding wall as that in Example 1, so the manufacturing cost is lower and the manufacturing is simpler.

EXAMPLE 9

In this example, the device is similar to that described in example 8, but further employs a thin bag containing the heat generating medium as in example 7. The thin bag is disposed in the space between the bottom wall and the curved cover.

In Examples 5–9, the chamber preferably has means for affixing the chamber onto human skin. One of the embodiment is an adhesive layer at the bottom of the chamber, similar to that in Example 1.

EXAMPLE 10

An alternative method for making heat generating medium involves storing a predetermined amount of activated carbon, iron powder, wood powder, and sodium chloride-in-water solution at or below a temperature low enough so that the sodium chloride-in-water solution is frozen. The substances are then mixed and ground at or below the same low temperature. The mixture resulted from the low temperature mixing and grinding is not expected to generate heat effectively because the water is in frozen state. The cold mixture is then loaded into a heat generating device, such as that in example 1, which is then sealed into a bag impermeable to air. After staying at room temperature for some time, water in the heat generating medium melts and reaches a homogeneous distribution in the heat generating medium in the heating device. To use, open the bag impermeable to air to expose the device to oxygen for heat generation.

What is claimed is:

1. A method for manufacturing a heating device capable of generating heat when exposed to oxygen, comprising the steps of:
    providing a sheet of material as the bottom wall of a chamber;
    providing a heat generating medium in a bag permeable to air and to an oxidation facilitating liquid, said heat generating medium being capable of generating heat when combined with the oxidation facilitating liquid comprising water and subsequently exposed to oxygen;
    placing said bag of heat generating medium without an oxidation facilitating liquid onto said bottom wall;
    disposing a predetermined amount of said oxidation facilitating liquid comprising water into said bag containing said heat generating medium;
    placing a sheet of material on said bag containing said heat generating medium and said bottom wall to form a cover, said cover having selected air permeability; and
    securing said cover onto said bottom wall to enclose said heat generating medium.

2. The method as claimed in claim 1, wherein said heat generating medium comprises iron powder, activated carbon, and a compound selected from the group of sodium chloride, potassium chloride, and magnesium chloride.

3. The method as claimed in claim 1, wherein said heat generating medium comprises wood powder.

4. The method as claimed in claim 1, wherein said bottom wall is a plastic tape.

5. The method as claimed in claim 1, wherein said securing of said cover onto said bottom wall comprises adhering said cover along an edge onto said bottom wall.

6. The method as claimed in claim 1, wherein said securing of said cover onto said bottom wall comprises heat sealing said cover along an edge onto said bottom wall.

7. The method as claimed in claim 1, wherein said cover with selected air permeability comprises a sheet of material substantially impermeable to air; said sheet defining a selected number of holes with selected size.

8. The method as claimed in claim 7, wherein said selected number of holes are covered with a membrane with selected air permeability.

9. The method as claimed in claim 7, wherein said cover comprises a sheet of material having thermal insulation properties.

10. The method as claimed in claim 1, wherein said heating device further comprises means for affixing itself onto human skin.

11. The method as claimed in claim 10, wherein said means for affixing comprises an adhesive area on said chamber.

12. A method for manufacturing a heating device capable of generating heat when exposed to oxygen, comprising the steps of:
    providing a sheet of material as the bottom wall of a chamber;
    providing a heat generating medium in a bag permeable to air and to an oxidation facilitating liquid, said heat generating medium being capable of generating heat when combined with the oxidation facilitating liquid comprising water and subsequently exposed to oxygen;
    placing said bag of heat generating medium without an oxidation facilitating liquid onto said bottom wall; and
    disposing a predetermined amount of said oxidation facilitating liquid comprising water onto said bag containing said heat generating medium whereby said oxidation facilitating liquid is absorbed through said bag and into said heat generating medium;
    placing a sheet of material on said bag containing said heat generating medium and said bottom wall to form a cover, said cover having selected air permeability; and
    securing said cover onto said bottom wall to enclose said heat generating medium.

13. The method as claimed in claim 12, wherein said heat generating medium comprises iron powder, activated carbon, and a compound selected from the group of sodium chloride, potassium chloride, and magnesium chloride.

14. The method as claimed in claim 12, wherein said heat generating medium comprises wood powder.

15. The method as claimed in claim 12, wherein said cover with selected air permeability comprises a sheet of material substantially impermeable to air; said sheet defining a selected number of holes with selected size.

16. The method as claimed in claim 15, wherein said selected number of holes are covered with a membrane with selected air permeability.

17. The method as claimed in claim 12, wherein said heating device further comprises means for affixing itself onto human skin.

* * * * *